US006335465B1

United States Patent
Golub (10) Patent No.: US 6,335,465 B1
(45) Date of Patent: *Jan. 1, 2002

(54) STERILIZED 5-AMINOLEVULINIC ACID (75) Inventor: Allyn Golub, Miramar, FL (US)

(73) Assignee: Dusa Pharmaceuticals, Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/486,604

(22) PCT Filed: Sep. 2, 1998

(86) PCT No.: PCT/US98/18181

§ 371 Date: May 30, 2000

§ 102(e) Date: May 30, 2000

(87) PCT Pub. No.: WO99/11604

PCT Pub. Date: Mar. 11, 1999

Related U.S. Application Data (63) Continuation of application No. 08/921,664, filed on Sep. 2, 1997, now Pat. No. 5,856,566.

(51) Int. Cl.$^7$ ............................................ C07C 229/24

(52) U.S. Cl. ..................................................... 562/567

(58) Field of Search ...................... 562/567; 204/157.15

(56) References Cited

U.S. PATENT DOCUMENTS

| 4,667,656 A | | 5/1987 | Yabe .............................. 128/6 |
| 5,234,940 A | | 8/1993 | Kennedy et al. ............. 514/410 |
| 5,422,093 A | | 6/1995 | Kennedy et al. ............ 424/9.61 |
| 5,380,935 A | | 1/1998 | Takeya et al. ............... 562/567 |
| 5,856,566 A | * | 1/1999 | Golub ......................... 562/567 |

FOREIGN PATENT DOCUMENTS

| DE | 42 28 106 A1 | 3/1994 |
| JP | 62-111954 | 5/1987 |
| JP | 7-238063 | 9/1995 |
| WO | WO 94/06424 | 3/1994 |
| WO | WO 95/07077 | 3/1995 |

OTHER PUBLICATIONS

Prasil & Marling, *Radiation Coloration of Glass–State of the Art*; Beta–Gamma 4/91 (1991).
Patil et al., *Chemical Effects Induced by Gamma Irradiated Salts in Aqueous Medium*, Int. J. Appl. Radiation, Isot. vol. 35, No. 6, pp 459–462 (1984).
Sabularse et al., *Physicochemical Characteristics of Brown Rice as Influenced by Gamma Radiation*, J. of Food Science, vol. 57, No. 1, pp 143–145 (1992).
Prasil & Marling, *Two Colors Out of One*, Beta–Gamma 2 + 3/91 (1991).
Baert et al., *Clinical Fluorescence Diagnosis of Human Bladder Carcinoma Following Low–Dose Photofrin Injection*, Urology,vol. 41, No. 4 (Apr. 1983).

Peng et al., *Build–up of Esterified Aminolevulinic–Acid–Derivate–Induced Porphyrin Fluorescence in Normal Mouse Skin*, J. of Photochemistry and Photobiology, vol. 34, No. 1, pp 95–96 (1996).
Kloek et al., *Prodrugs of 5–Aminolevulinic Acid for Photodynamic Therapy*, Photochemistry and Photobiology, vol. 64, No. 6, pp 994–1000 (1996).
Kriegmair et al., *Photodynamic Diagnosis (PDD) for Early Recognition of Carcinomata of the Bladder*, Endo World URO No. 17–E, 1995, Karl Storz GmbH & Co., Tuttlinger, Germany.
Reid, *Gamma Processing Technology: An Alternative Technology for Terminal Sterilization of Parentals*, PDA Journal of Pharmaceutical Science & Technology, vol. 49, No. 2, Mar.—Apr. 1995.
Bahnson RR. Editorial: *Urotheilial Malignancy—Much Promise But Little Progress*, J. Urology, vol. 155, 122 (1996).
Baumgartner R, Kriegmair M, Jocham D, Hofstetter A, Huber R,, Karg O, Häussinger K., *Photodynamic Diagnosis (PDD) of Early Stage Malignancies—Preliminary Results in Urology and Pneumology*, SPIE 1992; 1641: 107–112.
Baumgartner R, Kriegmair M, Lumper W, Riesenberg R, Stocker S, Sassy T, HofStetter A., *Delta–ALA–Assisted Fluorescence Detection of Cancer in the Urinary Bladder*, SPIE 1993:2081 (International Symposium on Biomedical Optics, Sep. 1993, Budapest, Hungary).
Chang S–C, MacRobert AJ, Bown SG., *The Biodistribution and Photodynamic Effect of Protoporphrin IX in Rat Urinary Bladders After Intravesical Instillation of 5–Aminolaevulinic Acid*, SPIE 1995; 2371:289–296.
Chang S–C, MacRobert AJ, Brown SG., *Biodistribution of Protoporphrin IX in Rat Urinary Bladder After Intravesical Instillation of 5–Aminolaevulinic Acid*, J. Urology 1996;155:1744–1748.

(List continued on next page.)

*Primary Examiner*—Sreeni Padmanabhan
*Assistant Examiner*—Brian J. Davis
(74) *Attorney, Agent, or Firm*—Foley & Lardner (57) ABSTRACT

Colored 5-aminolevulinic acid crystals useful for photodynamic therapy Eire disclosed. Preferably the colored 5-aminolevulinic acid crystals have the color imparted by irradiation of the crystals, such as gamma radiation. The colored ALA crystals are preferably pharmaceutically pure and sterile and can be contained in a sealed sterile container. Also disclosed is sterile aqueous ALA solution which includes the colored ALA crystals contained in water. Also disclosed is a method for preparing colored ALA crystals which includes exposing non-irradiated ALA crystals to a radiation source at a dose sufficient impart a color which is different than any color present in the non-irradiated crystals. Preferably the irradiation is sufficient to sterilize the ALA crystals. The sterile colored ALA crystals can be used in a kit for internal or external treatment and/or detection of a condition in a mammal, which includes the sterile, colored ALA crystals and sterile diluent, and in the case of internal treatment and/or detection optionally a catheter for administration of the ALA.

32 Claims, 7 Drawing Sheets

OTHER PUBLICATIONS

Chang S–C, MacRobert AJ, Bown SG., *Photodynamic Therapy on Rat Urinary Bladder with Intravesical Instillation of 5–Aminolaevulinic Acid: Light Diffusion and Histological Changes*, J. Urology 1996;155:1749–1753.

Forrer M, Glanzmann T, Mizeret J, et al., *Fluorescence Excitation and Emission Spectra of ALA Induced Protoporphyrin IX in Normal and Tumoraltissue of the Human Bladder*, SPIE 1995; 2324:84–88.

Iinuma S, Farshi, SS, Ortel B, Hasan T., *A mechanistic Study of Cellular Photodestruction with 5–Aminolevulinic Acid–Induced Porphyrin*, Br. J. Cancer 1994; 70:21–28.

Iinuma S, Bachor R, Flotte T, Hasan T., *Biodistribution and Photoxicity of 5–Aminolevulinic Acid Induced PpIX In An Orthotopic Rat Bladder Tumor Model*, J. Urology 1995;153:802–806.

Jichlinski PP, Mizeret J, Forrer M, Wagniere G, Van den Bergh H, Schmidlin F, Graber P, Leisinger H–J, *Les Tumeurs Superficielles de la Vessie*, Revue Medicals De La Suisse Ramanda, 115, 233–237, 1995.

Jichlinski P, Forrer M, Mizeret J, Braichotte D, Wagniéres G, Zimmer G, Guillou L, Schmidlin F, Graber P, Van den Bergh H, Leisinger H–J., *Usefulness of Fluorescence Photodetection of Neoplastic Urotheilial Foci in Bladder Cancer Following Intravesical Instillation of Delta–Aminolevulinic Acid (5–ALA)*, SPIE 1996; 2671:340–347.

Jichlinski P, Forrer M, Mizeret J, Glanzmann T, Ddraichotte D, Waigniéres G, Zimmer G, Guillou L, Schmidlin F, Graber P, Can den Bergh H, Leisinger H–J., *Clinical Evaluation of a Method for Detecting Superficial Transitional Cell Carcinoma of the Bladder by Light Induced Fluorescence of Protoporphyrin IX Following Topical Application of 5–Aminolevulinic Acid*, Lasers in Surgery and Medicine 1996; In review.

Jocham D, Baumgartner R, Fuchs N, Lenz H, Stepp H, Unsöld E., *Die Fluoreszenzdiagnose Porphyrin–Markierter Utothelialer Tumoren*, Urologe (A) 1989; 28:59–64.

Kriegmair M, Baumgartner R, Hofstetter A., *Intravesikale Instillation Von Delta–Aminolävulinsäure (ALA)—Eine Neue Methode Zur Photodynamischen Diagnostik Und Therapie*, Lasermedizin 1992; 8:83.

Kriegmair M, Baumgartner R, Knüchel R, Ehsan A, Steinbach P, Lumper W, Hofstädter F, Hofstetter A., *Photodynamische Diagnose Urothelialer Neoplasien Nach Intravesikaler Instillation Von 5–Aminolävulinsäure*, Urologe 1994; 33:270–275.

Kriegmair M, Baumgartner R, Knuechel R, Steinbach P, Ehsan A, Lumper W, Hofstädter F, Hofstetter A., *Fluorescence Photodetection of Neoplastic Urothelial Lesions Following Intravesical Instillation of 5–Aminolevulinic Acid*, Urology 1994; 44:836–841.

Kriegmair M, Baumgartner R, Ehsan A, Lumper W, Hofstetter A, Knuechel R, Steinbach P, Hofstädter F., *Detection of Early Bladder Cancer and Dysplasis by Fluorescence Cystoscopy*, J. Urology 1995; 153:457 A.

Kriegmair M, Stepp H, Steinbach P, Lumper W, Ehsan A, Stepp HG, Rick K, Knüchel R, Baumgartner R, Hofstetter A., *Fluroescence Cystoscopy Following Intravesical Instillation of 5–Aminolevulinic Acid: A New Procedure With High Sensitivity for Detection of Hardly Visible Urotheilial Neoplasias*, Urol 1995;55: 190–196.

Kriegmair M, Baumgartner R, Susanne S, Riesenberg R, Hofstetter A, Knuchel, R, Steinbach P., *Photodynamic Therapy Urothelial Cancer Following Intravesical Application of 5–Aminolaevulinic Acid in a Rat Bladder Tumor Model*, J. Urology 1994; 151:518A, abstract 1163.

Kriegmair M, Lumper W, Hofstetter A, Stenzl A, Höltl L, Bartsch G., *Photodynamic Therapy of Superficial Bladder Cancer Based on Intravesical Application of 5–Aminolevulinic Acid*, Proceedings of the American Urological Association 1996; 155:566A.

Kriegmair M, Stepp H, Baumgartner R, Hofstetter A, Knüchel R, Steinback P, Hofstädter F. Fluorescence controlled transurethral resection of bladder cancer following intravesical application of 5–aminolevulinic acid. Proceedings of the American Urological Association 1996;155: 655A.

Leveckis J, Burn JL, Brown NJ, Reed MWR., *Kinetics of Endogenous Protoporphyrin IX Induction by Aminolevulinic Acid: Preliminary Studies in the Bladder*, J. Urology 1994; 152:550–553.

Steinbach P, Kriegmair M, Baumgartner R., Hofstädter FZ., Knüchel R, *Intravesical Instillation of 5–Aminolevulinic Acid: the Fluorescent Metabolite is Limited to Urothelial Cells*, Urology 1994:44:676–681.

Steinbach P, Weingandt H, Baumgartner R, Kriegmair M, Hofstädter F, Knüchel R., *Cellular Fluorescence of the Endogenous Photosensitizer Protoporphyrin IX Following Exposure to 5–Aminolevulinic Acid*, Photochem, Photobiol. 1995;62:887–895.

Database CAPLUS on STN, Acc. No. 2000:146134, Golub et al., 'A calorimetric and spectroscopic investigation on the nature of gamma radiation induced coloration in 5–aminolevulinic acid.' Can. J. Anal. Sci. Spectrosc. 1999, 44(4), pp. 97–102.*

Kriegmair M, Baumgartner R, Knüchel R, Stepp H, Hofstädter F, Hofstetter A., *Detection of Early Bladder Cancer by 5–Aminolevulinic Acid Induced Porphyrin Fluorescence*, J. Urology 1996; 155:105–110.

Kreigmair M, Baumgartner R, Lumper W, Riesenberg R, Stocker S, Hofstetter A., *Fluorescence Cystoscopy Following Intravesical Instillation of Aminolevulinic Acid (ALA)*, J. of Urology, ALA 88th Annual Mtg. May 1993, 204A.

* cited by examiner

STERILIZED 5-AMINOLEVULINIC ACID

This application is a continuation of U.S. application 08/921,664, filed Sep. 2, 1997 and now U.S. Pat. 5,856,566. This application is a 371 of PCT/US98/18181 filed Sep. 2, 1998.

BACKGROUND OF THE INVENTION

1. Field of the Invention

This invention relates generally to the field of medicine, particularly pharmacotherapeutics and pharmacodetection, using photosensitizing agents and precursors thereof, especially 5-aminolevulinic acid, also known by the acronym "ALA." More specifically, this invention relates to colored ALA, especially sterilized ALA, which is stable under commercial conditions.

2. Description of Related Art

Photodynamic therapy involves the administration of a photosensitizing agent to a subject, including administration of a precursor of a photosensitizing agent such as ALA, and subsequent irradiation with light of the target cells or tissue of the subject. The photosensitizing agent preferentially accumulates in the target cells, namely cells or tissues that are more rapidly proliferating or growing than other cells or tissues in the target environment. The target cells may be more rapidly proliferating because they are malignant or non-malignant, of infective agent origin, e.g. viral, bacteria, parasite or fungal origin or not of infective agent origin; are normally hyperproliferative, such as the endometrium of pre-menopausal women, or are abnormally hyperproliferative, such as cells infected with an infective agent.

Although not intending to be bound by any particularly theory, it has been proposed that following administration of ALA, as a result of their more rapid proliferation, the target cells or tissue contain relatively greater concentrations of light sensitive porphyrins and thus are more sensitive to light.

The target cells or tissue containing sufficiently high concentrations of the photosensitizing agent, including the metabolites of ALA, selectively absorb greater amounts of light and can be selectively localized and distinguished from the adjacent cells or tissues via fluorescence, or damaged or destroyed. The effect of the light, as is well known in the art, depends on the photosensitizer selected; the wavelength, intensity and duration of administration of the light; and the timing of irradiation vis-a-vis the administration of the photosensitizing agent, and results in fluorescence or impairment or destruction of the target cells or tissue.

A variety of photosensitizing agents have been used for photodynamic therapy. The only commercially available photosensitizing agent is PhotofrinrP, a hemato porphyrin or HPD, sold by QLT Phototherapeutics, Inc. Vancouver, British Columbia. Synthetic porphyrins often have the disadvantage of having longer half-lives and lowered sensitivity to the rapidly growing cells as contrasted with normal cells than do naturally occurring porphyrins. The half-life of the photosensitizing agent is significant, since the buildup of excess porphyrins in the skin can result in reddening or burning of the skin.

An alternative to synthetic porphyrins are natural porphyrins. Natural porphyrins appear to have shorter half-lives than their synthetic counterparts, but are difficult to synthesize and more importantly, are unstable ex vivo under environmental conditions to which drugs are subjected in normal commercial distribution and storage channels.

A revolutionary discovery made in the late 1980's was that the naturally occurring amino acid ALA, a precursor in the metabolic pathway to heme, could be used in photodynamic therapy instead of synthetic porphyrins. ALA appears to act in the body as a precursor to naturally occurring, light sensitive porphyrins, which avoids the ex vivo problems associated with natural porphyrins noted above. This discovery has brought photodynamic therapy to a world wide interest level never before achieved with synthetic porphyrins.

ALA has a very short half-life, depending on the route of administration, is highly tissue specific and, as a naturally occurring amino acid, minimizes complications and side effects which arise when foreign substances are administered to the body. Unlike synthetic porphyrins, ALA also makes it possible to distinguish small or flat tumors, e.g. in the bladder, from normal tissues, visually by means of fluorescence excitation.

It is believed that ALA is converted by the cells and tissues in vivo or ex vivo into protoporphyrin IX and related endogenous biochemicals, which fluoresce or are degraded by light of the appropriate wavelength. The preferential accumulation of such naturally occurring porphyrins in rapidly growing cells permits the targeting of such cells.

Figure 1:
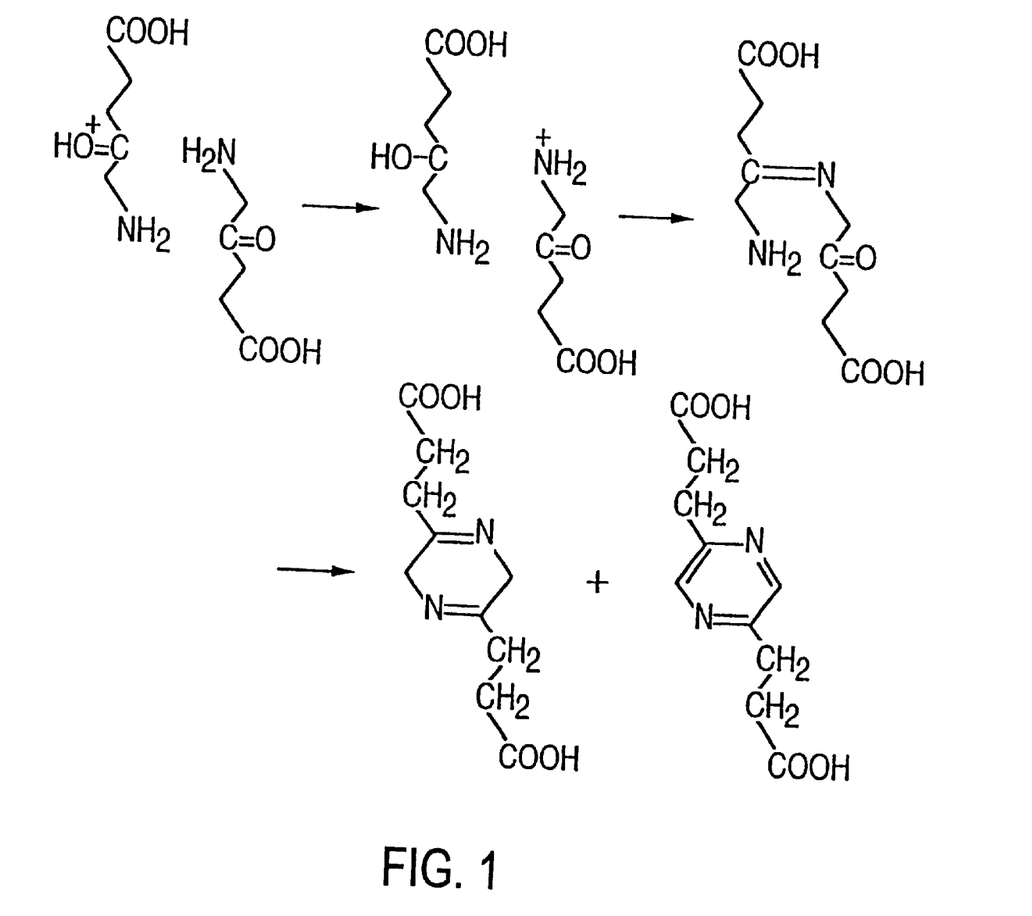
FIG. 1 depicts the degradation reaction pathway of ALA.

One of the roadblocks to the commercial use of ALA has been its extreme liability to destruction under ambient conditions. Aqueous solutions of ALA maintained under ambient conditions are progressively, degraded quite rapidly, resulting in degradation products, primarily 2,5-pyrazine dipropionic acid and intermediate degradation products which have not been able to be identified due to their transient nature. However, the intermediate degradation products are believed to include 2,5 (beta-carboxymethyl)-dihydropyrazine. FIG. 1 depicts the degradation of ALA to 2,5 (beta-carboxymethyl)-dihydropyrazine and then to 2,5-pyrazine dipropionic acid. Formulating ALA in nonaqueous creams and gels did not prevent this degradation. Even ALA pressure-sensitive adhesive mixtures did not totally stop oxidative reactions. Likewise, the preparation of pharmacological equivalents of ALA such as functional derivatives of the carboxylic acid group, substitution of the amino group, blocking of the oxo group or the use of simple or more complex acid addition, acid, base or neutral salts has not completely overcome this problem because the more stable the product, the greater effect there may be on the metabolism of the product in the body.

SUMMARY OF THE INVENTION

One object of the invention is to provide ALA which does not suffer from the problems of the known art, particularly the extreme degradation of ALA. Another object of the invention is to provide sterile stable ALA which is pharmacologically active and can be used in photodynamic therapy and detection. Still another object of the invention is to provide a method for making sterile, stable ALA which does not suffer from the problems of the known art. Yet another object of the invention is to provide a combination of ALA and an endoscope for internal use in a mammal. Still another object of the invention is to provide a method for using ALA in the detection and/or treatment of a condition in a mammal.

The foregoing objects and other objects are achieved according to one aspect of the present invention by colored 5-aminolevulinic acid, preferably 5-aminolevulinic acid HCl. In a preferred embodiment, the color is imparted by irradiation of crystals, preferably gamma radiation. According to another aspect of the invention, there has been provided colored 5-aminolevulinic acid crystals having an F-center point defect in the crystal lattice, where said F-center point defect imparts said color to the crystals.

According to still another aspect of the invention, there has been provided a sterile aqueous ALA solution comprising the colored ALA crystals according to the invention, contained in water. According to yet another aspect of the invention, there has been provided a sterile package comprising colored ALA crystals according to the invention in a sealed sterile container. According to yet another aspect of the invention, there has been provided a method for preparing colored ALA crystals according to the invention, which includes exposing non-irradiated ALA crystals to a radiation source at a dose sufficient to impart a color which is different than any color present in the non-irradiated crystals. According to still another aspect of the invention, there has been provided a kit for internal and/or external treatment and/or detection of a condition in a mammal, which includes the sterile colored ALA crystals according to the invention and a sterile diluent, preferably water. In one mode of internal treatment and/or detection, the kit optionally includes a catheter and optionally an endoscope.

According to still another aspect of the invention, there has been provided a method of administering 5-aminolevulinic acid in a stable form for internal and/or external mammal administration which comprises the administration of a solution of ALA derived from the colored ALA according to invention.

Further objects, features and advantages of the present invention will become apparent from consideration of the detailed preferred embodiments which follow.

BRIEF DESCRIPTION OF THE DRAWINGS

FIGS. 1–12 compare gamma irradiated with nonirradiated crystalline ALA. In the figures, "REF" denotes nonirradiated ALA and "IRR" denotes irradiated ALA.

DETAILED DESCRIPTION OF PREFERRED EMBODIMENTS

5-Aminolevulinic acid is also known as 5-aminolaevulinic acid, 6-aminolevulinic acid, δ-aminolaevulinic acid and 5-amino-4-oxopentanoic acid. 5-Aminolevulinic acid can be used as the salt, particularly a simple salt and especially the hydrochloride salt. 5-Aminolevulinic acid can also be used in the form of a precursor or product of 5-aminolevulinic acid. 5-Aminolevulinic acid can also be used in its pharmacologically equivalent form, such as an amide or ester. Examples of precursors and products of 5-aminolevulinic acid and pharmacologically equivalent forms of 5-aminolevulinic acid that can be used in the present invention are described in J. Kloek et al., *Prodruas of 5-Aminolevulinic Acid for Photodynamic Therapy*, Photochemistry and Photobiology, Vol. 64 No. 6, December 1996, pages 994–1000; WO 95/07077; Q. Peng et al., *Build-Up of Esterified Aminolevulinic-Acid-Derivative-Induced Porphyrin Fluorescence in Normal Mouse skin*, Journal of Photochemistry and Photobiology B: Biology, Vol. 34, No. 1, June 1996; and WO 94/06424, which are all incorporated by reference herein in their entirety. As used herein, all of these compounds, unless other wise noted, are referred to jointly and severally as "ALA."

As used herein, the term "sterilized" refers to a product which has been processed to make it suitable for internal pharmaceutical use.

As used herein, the term "colored" is defined as color that has been induced by irradiation. This is to be distinguished from non-irradiated ALA which is generally white, but in some instances may be off-white, probably due to the presence of varying amounts of degradation products.

As used herein, a "pharmaceutically pure" substance is defined as a substance which is suitable for therapeutic and detection use in humans and other mammals. Preferably, the pharmaceutically pure substance is labeled for therapeutic and detection use in humans and other mammals.

The present invention is based on the finding that sterile ALA can be made and prepared well in advance of its final use, despite the extreme degradation generally found with ALA as noted above. It was further and surprisingly found that despite the yellow color of irradiated crystalline ALA, the substance had not been degraded, despite the damaging effects that radiation, particularly gamma radiation, can have on thermodynamically unstable substances. In addition, it has been surprisingly found that the gamma irradiated material is stable for extended periods of time, at least one year, when stored in the sealed bottle in which it was irradiated.

The sterilized colored ALA crystals are preferably substantially free of impurities, such as degradation products and pyrogens, especially when intended for systemic administration. The amount of impurities is generally ≦2.0 wt %, preferably ≦1.0 wt %, and more preferably ≦0.5 wt %.

The crystalline ALA is colored to the naked eye by irradiation from a source which emits electromagnetic radiation, preferably gamma radiation or other ionizing radiation. For example when the hydrochloride salt of ALA is employed, the irradiation alters the appearance of the crystals to the naked eye from white or off-white to yellow. The intensity of the color, such as the yellow color for ALA HCl, is dependent on the crystalline form that is irradiated, such as the form as commercially supplied or a crystal that is further micronized. For example, when the ALA crystals are micronized, the irradiated ALA micronized crystals are less intensely colored than intact (i.e., non-micronized) ALA crystals. This is consistent with the F-center theory for colorization described below. The intensity is also dependent on the dosage of radiation that the crystalline ALA has been supplied with.

This color disappears after dissolution of the irradiated crystals and does not appear again upon recrystallization from an aqueous solution under ambient (i.e., room temperature and pressure) conditions. The colored crystalline irradiated ALA has not been distinguished in any chemical property from non-irradiated ALA, either by spectroscopic, chromatographic, solution pH or solubility profile, except for the color of the irradiated material. This is explained more fully below with respect to FIGS. 2 to 14.

Gamma irradiated ALA, as can be seen from FIGS. 2 through 14 is substantially physically and chemically the same, except for the color, as the non-irradiated ALA with respect to spectroscopic, chromatographic, solution pH and solubility profile. Although not intending to be bound by any theory, it appears that the color imparted by irradiation is due to F-centers.

Figure 2:
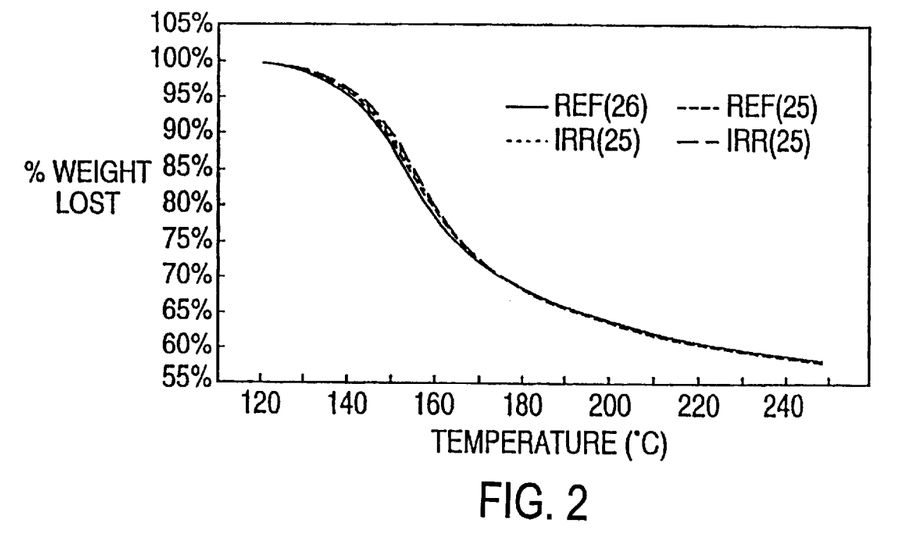
FIG. 2 compares thermogravimetic measurements.
Figure 3:
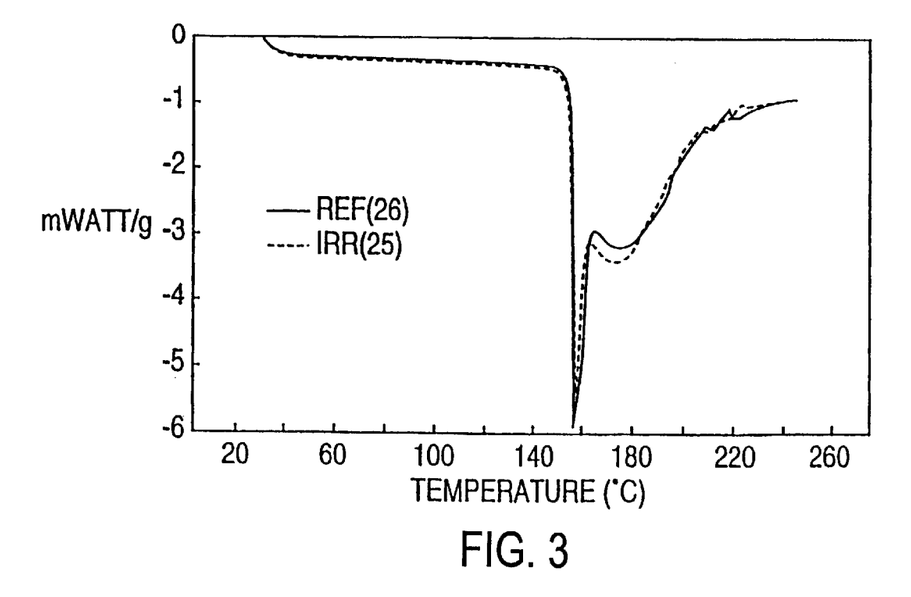
FIG. 3. compares differential scanning calorimetry measurements.
Figure 4:
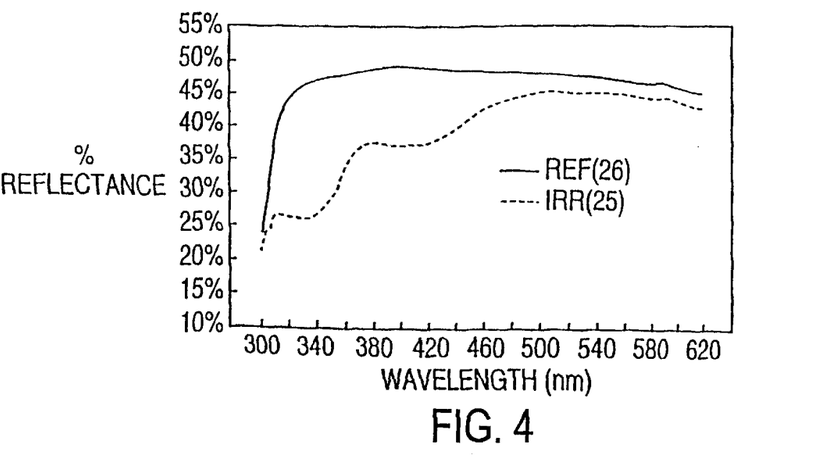
FIG. 4 compares reflectance spectra of solid samples.

The calorimetric measurements of FIGS. 2 and 3 indicate that any major structural differences are present in quantities of less than 1% of the total ALA amount, or that the type of any structural modification is such that the sensitivity of the calorimetric assay to the change is below the capacity of the instrumentation.

Figure 5:
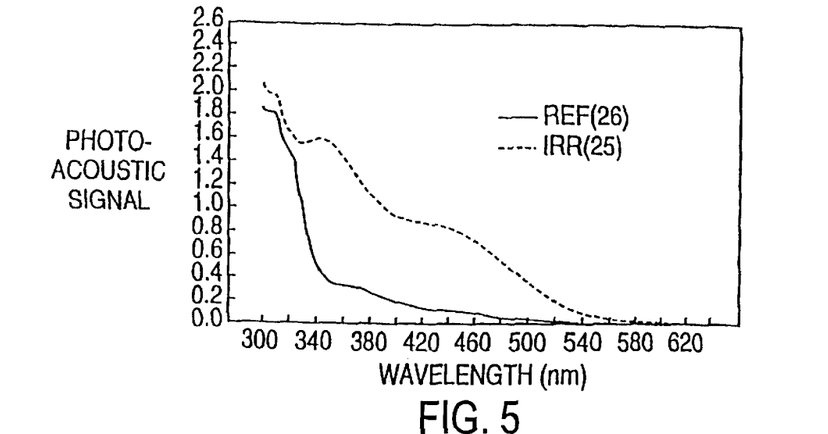
FIG. 5 compares the photoacoustic spectroscopy ("PAS") spectra.
Figure 6:
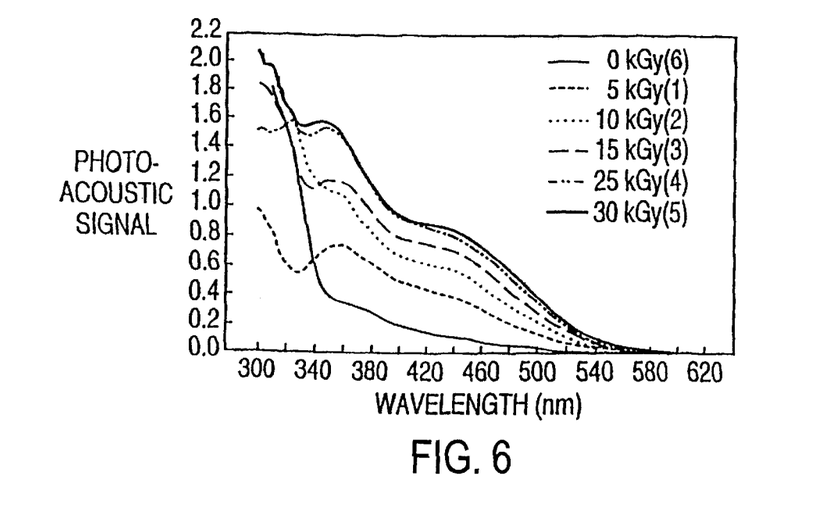
FIG. 6 compares the PAS spectra of gamma irradiated ALA as a function of the irradiation dose.
Figure 7:
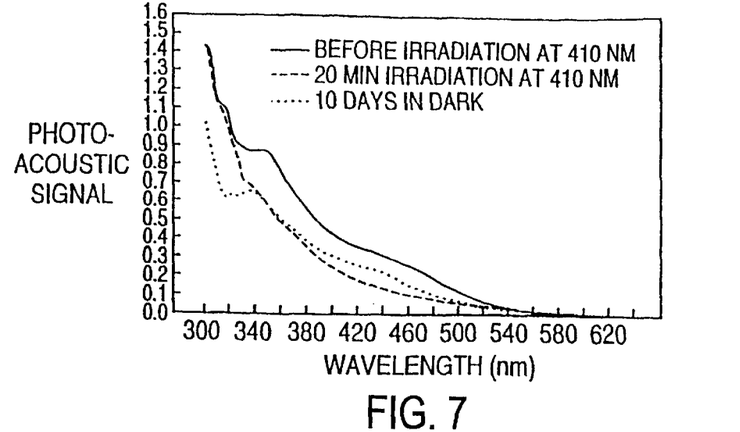
FIG. 7 compares the PAS spectra of a single sample of ALA before and 20 minutes after irradiation with visible light at 410 nm (2 mW cm$^{-2}$) and after a dark period of 10 days.

Spectral reflectance as shown in FIGS. 4 and 8–10 is very sensitive to spectral differences at or near the surface, while photoacoustic spectroscopy ("PAS") as shown in FIGS. 5–7 is sensitive to changes both at the surface and the interior of the crystal. Both of these techniques revealed significant spectral differences between the irradiated and nonirradiated reference samples of ALA in the solid crystalline phase. Since no differences were observed in the solution phase spectra, the yellow color of the irradiated material is likely to be a property of the crystalline solid only. Calorimetry failed to show gross crystal modifications, supporting the view that the crystal modifications are such that the overall crystal symmetry is not significantly affected.

Although not wishing to be bound by any theory, gamma radiation is known to cause point defects in substances such as alkali halides. Such alterations do not change the overall symmetry of the crystal, since they involve only the removal or relocation of small numbers of specific ions, while essentially leaving the major crystalline structure intact. The most common type of point defect caused by the ionizing radiation of the F-(farben)-center, which is a negative ion vacancy with one excess electron bound at the vacancy. The time required to fill the vacancy formed by the electrons is on the order of minutes to days, and is dependent on the diffusion rate of electrons in the crystal lattice. F-centers have been extensively studied and are characterized by one or more absorbance band(s) at higher wavelengths (lower energy) than that of the normal absorbance of the molecules surrounding the excess electron. These allowed, red-shifted bands are believed to stem from the excess electron gaining state function properties from the surrounding molecules in a symmetrical manner. The location of the UV-visible absorbance bands seen in FIGS. 4, 5 and 6, detected by both PAS and reflectance spectroscopy, is consistent with the F-centers.

Figure 8:
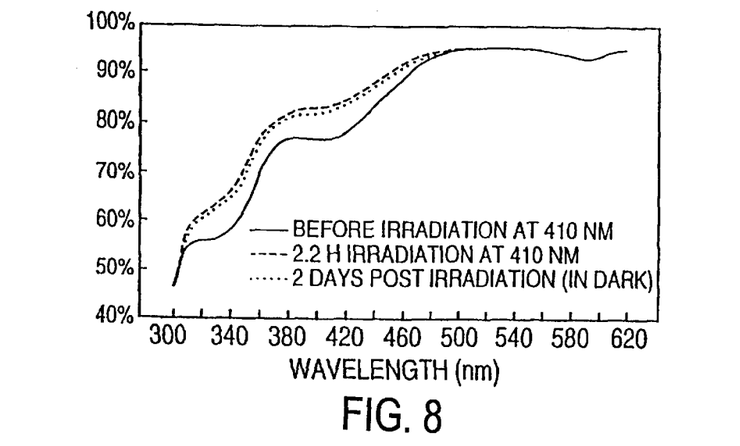
FIG. 8 compares the reflectance spectra before and 2.2 hours after irradiation with visible light at 410 nm (0.12 mW cm$^{-2}$) and after a 2 day dark period.
Figure 9:
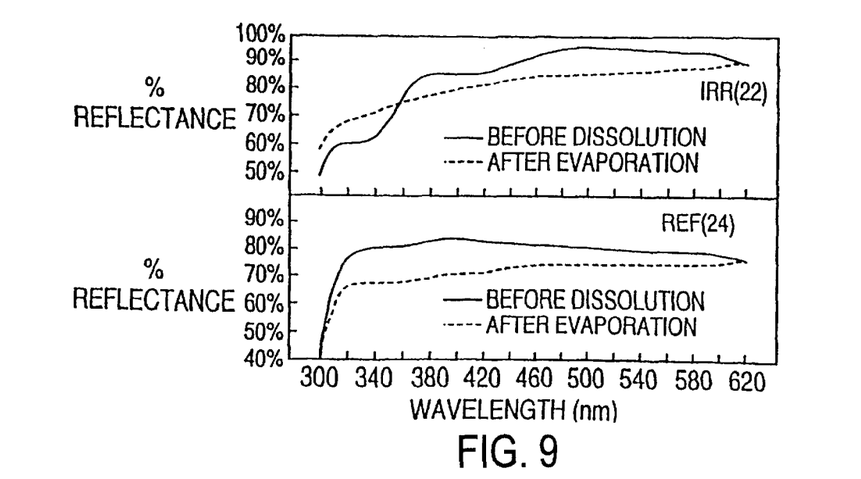
FIG. 9 compares the reflectance spectra before and after dissolution in methanol and evaporation of the solvent of ALA irradiated at 25 kGy.
Figure 10:
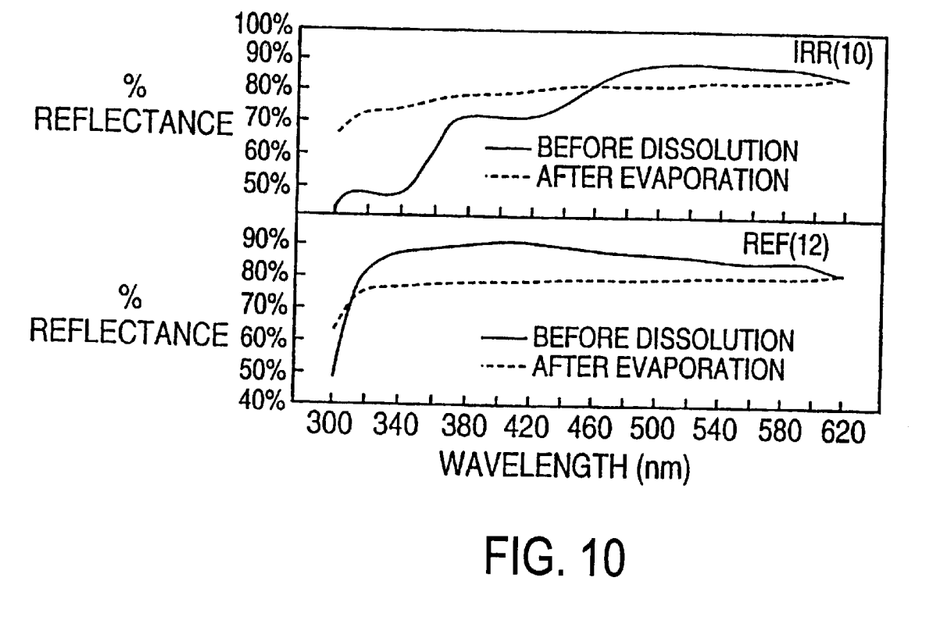
FIG. 10 compares the reflectance spectra prior to and after dissolution in methanol and evaporation of the solvent for a different set of samples than used in FIG. 9 irradiated at 25 kGy.
Figure 11:
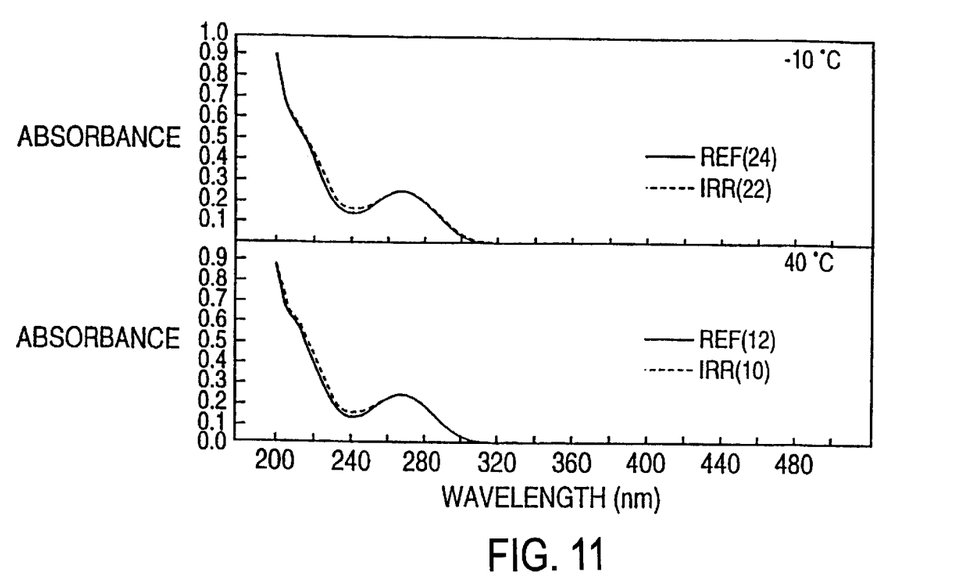
FIG. 11 compares the absorbance spectra of both gamma-irradiated and reference ALA in methanol for ALA which was stored at −10° C. and at 40° C.
Figure 12:
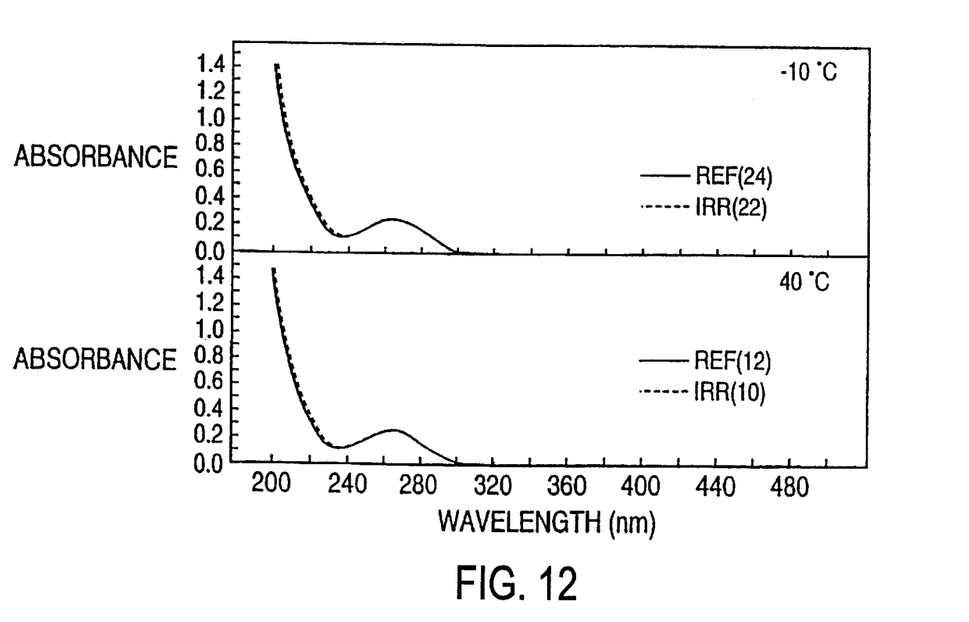
FIG. 12 compares the absorbance spectra of both 1s gamma-irradiated and reference ALA upon the first, and second dissolution in 0.2 M PBS, pH 5 for ALA stored at both −10° C. and 40° C.
Figure 13:
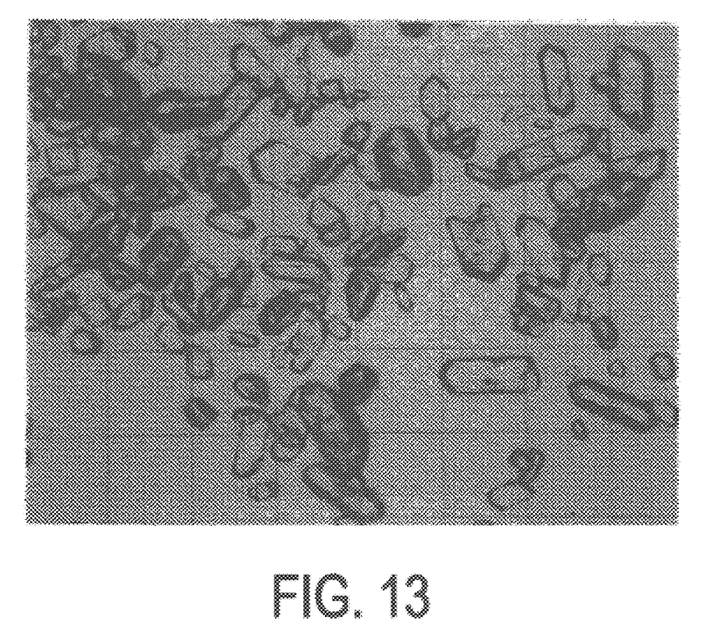
FIG. 13 shows a photograph taken at 4× magnification of gamma-irradiated colored ALA crystals.
Figure 14:
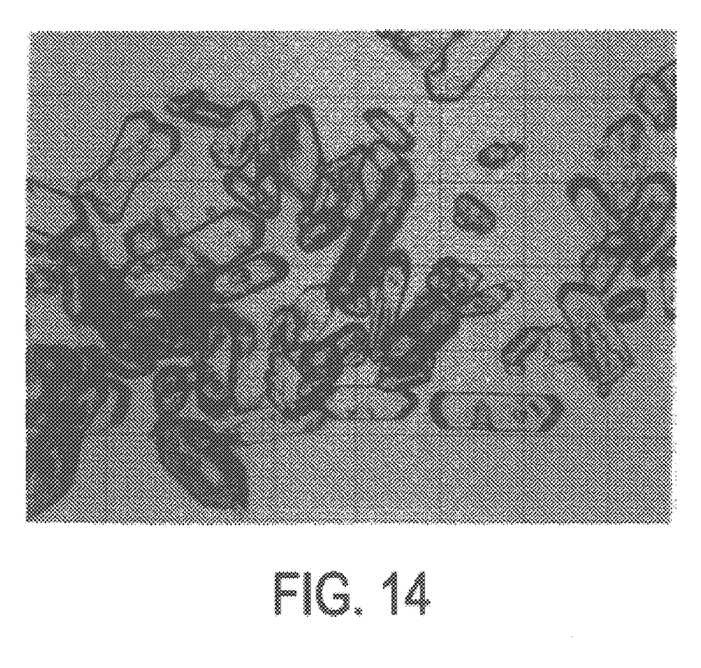
FIG. 14 shows a photograph taken at 4× magnification of non-irradiated ALA crystals.

The spectra shown in the photobleaching studies of FIGS. 7 and 8 is consistent with this F-center theory. The spectra depicted in FIGS. 9 through 12, suggest that the color is due to an F-center defect rather than preformed chemical degradation. FIGS. 13 and 14 indicate that no microscopic changes take place upon irradiation of the ALA.

Moreover, when ALA is irradiated, there is generally some delay before coloring of the crystal sets in. As noted above, the coloring is due to an ion being "kicked out" during irradiation, leaving a charged hole. The temporal delay in coloring is believed due to the basis of ion migration through the crystal lattice. This delay further supports the F-center theory.

Although the above measurements and analysis were carried out on ALA HCl, which produces a yellow color, it is fully expected that other crystalline forms of ALA would also experience non-degradation related coloring upon irradiation.

Another aspect of the invention provides methods for the preparation of sterile ALA suitable for internal use in human subjects and other mammals, namely by irradiating, particularly γ-irradiation, of ALA. Preferably, the irradiation is carried out in a sealed container, such that both the ALA and the container are sterilized during irradiation. The irradiation procedure sterilizes the ALA in the conventional sense. Sterilization by radiation, particularly gamma radiation is well known in the art and will not be discussed at length. More detailed information can be found in *Gamma Processing Technology: An Alternative Technolocv for Terminal Sterilization of Parenterals*, by B. D. Reid, PDA Journal of Pharmaceutical Science & Technology, vol. 49, no. 2, March–April 1995, pages 83–89, which is incorporated herein in its entirety.

The ALA is irradiated with a dose of radiation sufficient for sterilization. A sufficient dose of radiation can be determined by methods known to those skilled in the art. For example, after irradiating ALA with a selected dose, the ALA can be transferred to the appropriate media for encouraging the growth of viable microorganisms to determine if sterilization is sufficiently complete.

For most applications using gamma irradiation, a dose of 5 kilograys or greater has been found to provide sufficient sterilization. However, as noted above, the crystalline ALA has been surprisingly found to resist degradation even at high doses of gamma radiation. Thus, it is possible to provide a dose of 25 kilograys or greater, without detectable degradation of the ALA. This is significant, in that the United States Food and Drug Administration's ("FDA") level of gamma irradiation for "overkill" is 25 kilograys. This is a level at which the FDA presumes, without evidence, that virtually all microorganisms have been killed.

The present invention also provides for methods of using the sterilized ALA in photodynamic therapy internally or externally on the tissues or cells of a mammal. For external use, the sterilized ALA may be applied by an applicator. For internal use, application may be orally, intravenously or administration by a catheter. For example, the administration of the ALA can be on internal surfaces of the body of the subject, typically in conjunction with an endoscope coupled to a light source. Numerous publications discuss photodynamic therapy, see e.g. Kriegmair et al., "Photodynamic Diagnosis (PDD) for Early Recognition of Carcinomata of the Bladder", ENDO World Uro No. 17-E, 1955, a publication of Karl Storz Gmbh & Co. and the equipment referred to therein. See also:

1. Bahnson RR. Editorial: Urothelial malignancy—Much promise but little progress. J. Urology 1996; 155:122.
2. Baumgartner R, Kriegmair M, Jocham D, Hofstetter A, Huber R, Karg O, Haüssinger K. Photodynamic diagnosis (PDD) of early stage malignancies—Preliminary results in urology and pneumology. SPIE 1992; 1641:107–112.
3. Baumgartner R, Kriegmair M, Lumper W, Riesenberg R, Stocker S, Sassy T, Hofstetter A. ALA-assisted fluorescence detection of cancer in the urinary bladder. SPIE 1993:2081 (International Symposium on Biomedical Optics, September 1993, Budapest, Hungary)
4. Chang S-C, MacRobert A J, Bown S G. The biodistribution and photodynamic effect of protoporphyrin IX in rat urinary bladders after intravesical instillation of 5-aminolaevulinic acid. SPIE 1995; 2371:289296.
5. Chang S-C, MacRobert A J, Bown S G. Biodistribution of protoporphyrin IX in rat urinary bladder after intravesical instillation of 5-aminolaevulinic acid. J. Urology 1996;155:1744–1748.
6. Chang S-C, MacRobert A J, Bown S G. Photodynamic therapy on rat urinary bladder with intravesical instillation of 5-aminolaevulinic acid: light diffusion and histological changes. J. Urology 1996;1 55:1749–1753.
7. Forrer M, Glanzmann T, Mizeret J, et al. Fluorescence excitiation and emission spectra of ALA induced protoporphyrin IX in normal and tumoral tissue of the human bladder. SPIE 1995; 2324:84–88.
8. Iinuma S, Farshi, S S, Ortel B, Hasan T. A mechanistic study of cellular photodestruction with 5-aminolevulinic acid-induced porphyrin. Br. J. Cancer 1994; 70:21–28.
9. Iinuma S, Bachor R, Flotte T, Hasan T. Biodistribution and photoxicitiy of 5-aminolevulinic acid induced PpIX in an orthotopic rat bladder tumor model. J. Urology 1995; 1 53:802–806.
10. Jichlinski P P, Mizeret J, Forrer M, Wagniere G, Van den Bergh H, Schmidlin F, Graber P, Leisinger H-J. Les tumeurs superficielles de la vessie. Rappel pathologique et clinique, et presentation d'une nouvelle méthode diagnostique: la photodétection par fluorescence des carcinomas à épithélium de transition baste sur l'induction de protoporphyrine IX par l'acide delta-aminolévulinique (5-ALA).
11. Jichlinski P, Forrer M, Mizeret J, Braichotte D, Wagnie­fres G, Zimmer G, Guillou L, Schmidlin F, Graber P, Van den Bergh H, Leisinger H-J. Usefulness of fluorescence photodetection of neoplastic urothelial foci in bladder cancer following intravesical instillation of delta-aminolevulinic acid (5-ALA). SPIE 1996; 2671:340–347.
12. Jichlinski P, Forrer M, Mizeret J, Glanzmann T, Ddra­ichofte D, Wagniéres G, Zimmer G, Guillou L, Schmidlin F, Graber P, Van den Bergh H, Leisinger H-J. Clinical evaluation of a method for detecting superficial transitional cell carcinoma of the bladder by light induced fluorescence of protoporphyrin IX following topical application of 5-aminolevulinic acid. Preliminary results. Lasers in Surgery and Medicine 1996; ln review.
13. Jocham D, Baumgartner R, Fuchs N, Lenz H, Stepp H, Unsöld E. Die fluoreszenzdiagnose porphyrinmarkierter utothelialer tumoren. Urologe (A) 1989; 28:59–64.
14. Jocham D. Photodynamische verfahren in der urologie. Urologe 1994; 3:547–552.
15. Kriegmair M, Baumgartner R, Hofstetter A. Intravesikale instillation von deltaaminolävulinsäure (ALA)—eine neue methode zur photodynamischen diagnostik und therapies Lasermedizin 1992; 8:83.
16. Kriegmair M, Baumgartner R, Knüchel R, Ehsan A, Steinbach P, Lumper W, Hofstädter F, Hofstetter A. Photodynamische diagnose urothelialer neoplasien nach intravesikaler instillation von 5-aminolavulinsaure. Urologe 1994; 33:270–275.
17. Kriegmair N, Baumgartner R., Knuechel R, Steinbach P, Ehsan A, Lumper W, Hofstädter F, Hofstetter A. Fluorescence photodetection of neoplastic urothelial lesions following intravesical instillation of 5-aminolevulinic acid. Urology 1994; 44:836–841.
18. Kriegmair M, Baumgartner R, Ehsan A, Lumper W, Hofstetter A, Knuechel R, Steinbach P, Hofstädter F. Detection of early bladder cancer and dysplasia by fluorescence cystoscopy. J. Urology 1995; 153:457 A.
19. Kriegmair M, Stepp H, Steinbach P, Lumper W, Ehsan A, Stepp HG, Rick K, Kntichel R, Baumgartner R, Hofstetter A. Fluorescence cystoscopy following intravesical instillation of 5-aminolevulinic acid: a new procedure with high sensitivity for detection of hardly visible urothelial neoplasias. Urol lnt 1995;55: 190–196.
20. Kriegmair M, Baumgartner R, Knuichel R, Stepp H, Hofstädter F, Hofstadter A. Detection of early bladder cancer by 5-aminolevulinic acid induced porphyrin fluorescence. J. Urology 1996; 155:105–110.
21. Kriegmair M, Baumgartner R, Lumper W, Waidelich R. Hofstetter A. Early clinical experience with 5-aminolevulinic acid for photodynamic therapy of superficial bladder cancer. British Journal Urology 1996; Accepted for publication.
22. Kriegmair M, Baumgartner R, Lumper W, Riesenberg R, Stocker S, Hofstetter A. Fluorescence cystoscopy following intravesical instillation of aminolevulinic acid (ALA). 204 A.
23. Kriegmair M, Baumgartner R, Susanne S, Riesenberg R, Hofstetter A, Knuchel, R, Steinbach P. Photodynamic treatment of urothelial cancer following intravesical application of 5-aminolaevulinic acid in a rat bladder tumor model. J. Urology 1994, 151: 518A, abstract 1163.
24. Kriegmair M, Lumper W, Hofstetter A, Stenzl A, Höltl L, Bartsch G. Photodynamic therapy of superficial bladder cancer based on intravesical application of 5-aminolevulinic acid. Proceedings of the American Urological Association 1996; 155: 566A.
25. Kriegmair M, Stepp H, Baumgartner R, Hofstetter A, Kn üchel R, Steinbach P, Hofstädter F. Fluorescence controlled transurethral resection of bladder cancer following intravesical application of 5-aminolevulinic acid. Proceedings of the American Urological Association 1996;155: 655A.
26. Leveckis J, Burn J L, Brown N J, Reed M W R. Kinetics of endogenous protoporphyrin IX induction by aminolevulinic acid: preliminary studies in the bladder. J. Urology 1994; 152:550–553.
27. Moore R B, Miller G G, Brown K, Bhatnagar R, Tulip J, McPhee MS. Urothelial conversion of 5-aminolevulinic acid to protoporphyrin-IX following oral or intravesical administration. SPIE 1995; 2371:284–288.
28. Novo M, Hüttmann G. Diddens H. Chemical instability of 5-aminolevulinic acid used in the fluorescence diagnosis of bladder tumours. J. Photochem. Photobiol. B: Biol. 1996; Accepted for publication.
29. Rodriguez M, Hüttmann G, Diddens H. Chemical instability of 5 aminolevulinic acid (ALA) in aqueous solution. SPIE 1995; 2371:204–209.
30. Thomas S, Kaspers I, Schmitt-Conrad M, Svanberg K, Diddens H, Hüttman G, Jocham D. Photodynamic imaging of urothelial bladder cancer after topical instillation of 5-aminolevulinic acid (5-ALA), 5th Biennial Meeting of the International Photodynamic Association, September 1994, Amelia Island, Fla. (USA).
31. Steinbach P, Kriegmair M, Baumgartner R. Hofstädter FZ. Knüchel R. Intravesical instillation of 5-aminolevulinic acid: the fluorescent metabolite is limited to urothelial cells. Urology 1994: 44:676–681.
32. Steinbach P, Weingandt H, Baumgartner R, Kriegmair M, Hofstädter F, Knüchel R. Cellular fluorescence of the endogenous photosensitizer protoporphyrin IX following exposure to 5-aminolevulinic acid. Photochem. Photobiol. 1995;62:887–895.

All of the above references are incorporated herein in their entireties. Other photodynamic therapy or photodetection uses include treatment of actinic keratoses, hair removal, treatment of acne and endometrial ablation.

Endoscopes coupled to a light source for use in photodynamic therapy are sold commercially but can be especially designed for use with ALA and its precursors. Suitable endoscopes for use with a light source are commercially available, e.g. from Karl Storz Gmbh & Co., Tuttligen, Germany; Circon ACMI; Olympus; and Richard Wolf. Another suitable endoscope is described in U.S. Pat. No. 5,441,531, incorporated herein by reference in its entirety.

This invention also provides for commercial kits containing sterilized ALA, a sterile diluent such as an aqueous buffer solution, and, optionally a catheter for administering the ALA solution. An endoscope coupled to a light source such as those described above, for use in detection or treatment of the cells or tissues in which the ALA preferentially accumulates can also be included in the kit. Preferably instructions on the use of the ALA are packaged with the kits.

Reference will now be made to the following non-limiting examples.

EXAMPLES 1–4 AND COMPARATIVE EX. 1

ALA hydrochloride salt was obtained from Sochinaz, S.A., Vionnez, Switzerland. 1.65 grams of ALA hydrochloride salt was placed into 60 ml glass vials. 360 vials of crystalline non-irradiated ALA were prepared. of these, 225 vials were sealed under ambient conditions, and were irradiated with gamma radiation as shown in Table 1.

TABLE 1

| Example | no. of vials | conditions | target dose (KGys) | color |
| --- | --- | --- | --- | --- |
| 1 | 45 | crystalline, atmospheric, room | 15 | yellow |
| 2 | 45 | same as Ex. 1 | 30 | yellow |
| 3 | 45 | crystalline, atmospheric, packed in dry ice | 15 | yellow |
| 4 | 45 | same as Ex. 3 | 30 | yellow |
| Comp.Ex.1 | 45 | same as Ex. 1 | 0 | off white |

EXAMPLES 5–6 AND COMPARATIVE EX. 2

The other 135 vials as prepared above were sealed under an argon atmosphere and were irradiated as shown in Table 2.

TABLE 2

| Example | no. of vials | conditions | target dose (KGys) | color |
| --- | --- | --- | --- | --- |
| 5 | 45 | crystalline, argon atmosphere, room temperature | 15 | yellow |
| 6 | 45 | same as Ex. 5 | 30 | yellow |
| Comp. Ex. 2 | 45 | same as Ex. 5 | 0 | off white |

EXAMPLES 7–10 AND COMPARATIVE EXS. 3 AND 4

Crystalline ALA was first micronized by pulverizing into fine particles a few $\mu$m in diameter by a jet mill by Micro-Macinazione, S.A. to determine if further reducing the crystalline size would have any effect on the color of the irradiated ALA. After micronization, 1.65 grams of ALA hydrochloride salt was placed into 60 ml glass vials. A total of 270 vials of crystalline non-irradiated ALA were prepared. Of these, 135 vials were sealed under ambient conditions and irradiated with gamma radiation as shown in Table 3. The other 135 vials were sealed under an argon atmosphere and irradiated with gamma radiation as shown in Table 3.

TABLE 3

| Example | no. of vials | conditions | target dose (KGys) | color |
| --- | --- | --- | --- | --- |
| 7 | 45 | micronized crystalline, atmospheric, room temperature | 15 | yellow |
| 8 | 45 | micronized crystalline, atmospheric, room temperature | 30 | yellow |
| Comp. Ex. 3 | 45 | micronized crystalline, atmospheric, room temperature | 0 | off white |
| 9 | 45 | micronized crystalline, argon, room temperature | 15 | yellow |
| 10 | 45 | micronized crystalline, argon, room temperature | 30 | yellow |
| Comp. Ex. 4 | 45 | micronized crystalline, argon, room temperature | 0 | off white |

Subsequent analysis of the type described above with respect to FIGS. 2–14, confirmed that there was no discernible difference in structure or pharmacological activity between the irradiated examples and the non-irradiated control comparative examples.

The gamma irradiation also results in a darkening of the glass bottle used to contain the ALA. Presumably the darkening is due to impurities in the glass that do not affect its pharmaceutical acceptability. In fact, this darkening is an advantage since it shades the bottle contents from direct light.

Other embodiments of the invention will be apparent to those skilled in the art from consideration of the specification and practice of the invention disclosed herein. It is intended that the specification be considered as exemplary only, with the true scope and spirit of the invention being indicated by the following claims.

What is claimed is:

1. Colored 5-aminolevulinic acid crystals, wherein said color is imparted by irradiation of the crystals.

2. The yellow ALA crystals according to claim 1, wherein said crystals are pharmaceutically pure and sterile.

3. The yellow ALA crystals according to claim 1, wherein said irradiation is ganmna irradiation.

4. The yellow ALA crystals according to claim 3, wherein said gamma irradiation is sufficient to sterilize said crystals.

5. The yellow ALA crystals according to claim 4, wherein said gamma irradiation provides a dose of at least 5 kilograys.

6. The yellow ALA crystals according to claim 4, wherein said gamma irradiation provides a dose of at least 25 kilograys.

7. The yellow ALA crystals according to claim 1, wherein said ALA contains less than 2.0 wt % impurities.

8. The yellow ALA crystals according to claim 1, wherein said ALA contains less than 1.0 wt % impurities.

9. The yellow ALA crystals according to claim 1. wherein said ALA contains less than 0.5 wt % impurities.

10. The yellow ALA crystals according to claim 1, wherein said crystals dissolved in an aqueous solution have substantially the same spectroscopic, chromatographic, solution pH and solubility profile as nonirrmdiated 5-aminolevulinic acid.

11. A sterile ALA solution comprising the colored ALA crystals according to claim 2, contained in a diluent.

12. A sterile package comprising colored ALA crystals according to claim 2 in a scaled sterile container.

13. A sterile package according to claim 12, wherein the container is sterilized by irradiation.

14. A method for preparing colored ALA crystals according to claim 1, comprising exposing non-irradiated ALA crystals to a radiation source at a dose sufficient to inpart a color which is different than any color present in the non-irradiated crystals.

15. A method for preparing colored ALA crystals according to claim 14 further comprising: placing non-irradiated ALA crystals into a container; scaling said container; and exposing the non-irradiated ALA crystals and the container to a radiation source at a dose sufficient to impart a color which is different than any color present in the non-irradiated crystals and is sufficient to sterilize said crystals and container.

16. A kit for internal treatment and/or detection of a condition in a mammal, comprising the sterile colored ALA crystals according to claim 2 and sterile diluent.

17. A kit according to claim 16, further comprsing a catheter.

18. A kit according to claim 16, wherein the colored ALA crystals are packaged in a sterile container.

19. A method of admrinisterig 5-aminolevulinic acid in a stable form for internal and/or external mammal administration which comprises the administration of a solution of ALA derived from the colored ALA according to claim 1.

20. Yellow 5-aminolevuinic acid crystals comprising an F-center point defect in the crystal lattice, wherein said F-center point defect imparts said yellow color to the crystals.

21. A method for targeting hyperproliferative cells or tissues comprising:

administering a solution of ALA derived from the colored ALA according to claim 1 to the hyperproliferative cells or tissues of a subject in need thereof; and irradiating the target cells or tissues with light for a time sufficient to damage or destroy the hyperproliferative cells or tissues.

22. A method for targeting malignant hyperproliferative cells or tissues comprising:

administering a solution of ALA derived from the colored ALA according to claim 1 to the malignant hyperproliferative cells or tissues of a subject; and irradiating the target cells or tissues with light for a time sufficient to damage or destroy the malignant hyperproliferative cells or tissues.

23. A method for targeting cells or tissues infected with an infective agent comprising:

administering a solution of ALA derived from the colored ALA according to claim 1 to the cells or tissues infected with an infective agent of a subject; and irradiating the target cells or tissues with light for a time sufficient to damage or destroy the cells or tissues infected with an infective agent wherein the infective agent is of a viral, bacteria, parasite, or fungal origin.

24. A method for targeting cells or tissues of viral, bacteria, parasite or fungal origin comprising:

administering a solution of ALA derived from the colored ALA according to claim 1 to the cells or tissues of viral, bacteria, parasite or fungal origin; and irradiating the target cells with light for a time sufficient to damage or destroy the cells or tissues of viral, bacteria, parasite or fungal origin.

25. A method for treating actinic keratoses comprising:

administering a solution of ALA derived from the colored ALA according to claim 1 to an afflicted region of a subject in need thereof; and irradiating the afflicted region with light for a time sufficient to treat the actinic keratoses.

26. A method for hair removal comprising:

administering a solution of ALA derived from the colored ALA according to claim 1 to a region of a subject in need of hair removal; and irradiating the region with light for a time sufficient to remove hair.

27. A method for treating acne comprising: administering a solution of ALA derived from the colored ALA according to claim 1 to an acne containing region of a subject; and irradiating the region with light for a time sufficient to treat acne.

28. A method for treatment of endometrial ablation comprising:

administering a solution of ALA derived from the colored ALA according to claim 1 to a region of a subject in need thereof; and irradiating the region with light for a time sufficient to treat endometrial ablation.

29. A sterile package comprising colored ALA crystals according to claim 2 in a sealed sterile container, wherein the container is darkened by the irradiation.

30. A kit according to claim 16, further comprising a endoscope.

31. A method of administering 5-aminolevulinic in a stable form for external mammal administration which comprises applying a solution of ALA derived from the colored ALA according to claim 1 with an applicator to a subject in need thereof.

32. A method for treating bladder cancer comprising:

administering a solution of ALA derived from the colored ALA according to claim 1 to a bladder containing malignant cells; and irradiating the bladder with light for a time sufficient to damage or destroy the malignant cells.

* * * * *

UNITED STATES PATENT AND TRADEMARK OFFICE
CERTIFICATE OF CORRECTION

PATENT NO. : 6,335,465 B1  Page 1 of 1
APPLICATION NO. : 09/486604
DATED : January 1, 2002
INVENTOR(S) : Allyn Golub It is certified that error appears in the above-identified patent and that said Letters Patent is hereby corrected as shown below:

IN THE CLAIMS

Column 11, line 2 should read

1. Yellow ~~Colored~~ 5-aminolevulinic acid crystals, wherein said color is imparted by irradiation of the crystals.

Signed and Sealed this

Twenty-eighth Day of August, 2007

JON W. DUDAS
*Director of the United States Patent and Trademark Office*